United States Patent [19]

Kimble et al.

[11] Patent Number: 4,650,568

[45] Date of Patent: Mar. 17, 1987

[54] TRITHIOCARBONATES AS DEPRESSANTS IN ORE FLOTATION

[75] Inventors: Kenneth B. Kimble; Clarence R. Bresson; Harold W. Mark, all of Bartlesville, Okla.

[73] Assignee: Phillips Petroleum Company, Bartlesville, Okla.

[21] Appl. No.: 715,222

[22] Filed: Mar. 22, 1985

[51] Int. Cl.[4] ....................... B03D 1/14; C07C 153/00; C09K 3/00

[52] U.S. Cl. .................................... 209/167; 558/243; 252/61

[58] Field of Search .................... 260/455 B; 558/243; 209/167; 252/61

[56] References Cited

U.S. PATENT DOCUMENTS

| | | | |
|---|---|---|---|
| 2,600,737 | 6/1952 | Crouch et al. | 558/243 |
| 4,341,715 | 7/1982 | Parlman et al. | 558/243 |
| 4,459,237 | 7/1984 | Bresson et al. | 558/243 |
| 4,510,050 | 4/1985 | Parlman et al. | 558/243 |
| 4,533,467 | 8/1985 | Kimble et al. | 260/455 B |

OTHER PUBLICATIONS

Maatschappy, C.A.: 33: 7318–9.

*Primary Examiner*—Henry R. Jiles
*Assistant Examiner*—Robert C. Whittenbaugh
*Attorney, Agent, or Firm*—John R. Casperson

[57] ABSTRACT

Polyhydroxytrithiocarbonates can be used as depressants in ore flotation.

19 Claims, No Drawings

TRITHIOCARBONATES AS DEPRESSANTS IN ORE FLOTATION

In one aspect, this invention relates to novel compositions. In another aspect, the invention relates to the use of certain compositions. In another aspect this invention relates to the use of certain compositions in flotation processes for recovering minerals from their ores. In another aspect of the invention it relates to the use of flotation agents and flotation depressants in the recovery of minerals from their ores.

Froth flotation is a process for concentrating minerals from ores. In a froth flotation process, the ore is crushed and wet ground to obtain a pulp. Additives such as collecting or mineral flotation agents and frothing agents are added to the pulp to assist in subsequent flotation steps in separating valuable minerals from the undesired portions of the ore. The pulp is then aerated to produce a froth at the surface. The minerals which adhere to the bubbles or froth are skimmed or otherwise removed and the mineral-bearing froth is collected and further processed to obtain the desired minerals. Frequently, other chemicals are added to the separated mineral-bearing froth to assist in subsequent separations particularly when significant proportions of two or more minerals are present in the separated mineral-bearing froth. Such chemicals are known as depressants. These materials are sometimes referred to more appropriately as deactivators and are used selectively to separate one type of mineral from another type of mineral.

OBJECTS OF THE INVENTION

It is one object of the invention to provide compositions which can be used, for example as flotation depressants in ore flotation processes.

It is another object to provide a process for the recovery of substances from ores.

It is still another object of this invention to provide ore separation process employing a treating agent.

Other aspects and objects of this invention will become apparent upon reading this specification and the appended claims.

DESCRIPTION OF THE INVENTION

The novel compositions having a use as treating agents herein are believed to contain water soluble salts of polyhydroxy-substituted hydrocarbyltrithiocarbonates conforming to the general formula:

$$(HO)_n-R'-CH_2-S-\overset{\overset{S}{\|}}{C}-S-Y \qquad (I)$$

wherein R' is a $C_{2-21}$ organic moiety; and Y is a Group IA or IIA metal ion or an ammonium ion, preferably ammonium or Group IA metal ion since Group IIA metal salts tend toward insolubility, and n is an integer of from 2 to 22. A preferred group of compositions are the salts of polyhydroxyhydrocarbyltrithiocarbonates conforming to the formula:

$$CH_2OH-\underset{}{\overset{(OH)_n}{\overset{|}{R}}}-CHOH-CH_2-S-\overset{\overset{S}{\|}}{C}-S-Y \qquad (II)$$

where R if present is a $C_0$–$C_{20}$ organic moiety, Y has the above meaning and n is 0 to 20.

Preferably, R is hydroxyalkyl having from 1 to 6 carbon atoms and n is 0 to 3.

One technique for preparing compositions according to the invention results from combining ingredients in an aqueous reaction medium in a manner represented by the equation:

$$(HO)_n-R-CH_2-SH + CS_2 + YOH$$

$$(HO)_n-R'-CH_2-S\overset{\overset{O}{\|}}{C}-SY + H_2O$$

wherein R' and Y have the designations recited above and n is an integer of from 2 to 22.

The organic moiety, R' in the reagents of the invention can be any organic moiety containing up to about 22 carbon atoms containing a plurality of hydroxyl groups. Mixtures of the thus characterized treating agent are suitable for use in the invention. Preferably, R has an alkyl backbone and contains 2 to 15 carbon atoms and 2 to 4 hydroxyl groups.

At least one Y substituent is associated with an anionic sulfur atom of the trithiocarbonate. While Y may be an ammonium ion or any Group IA or Group IIA metal ion, it is preferred that Y be a Group IA metal ion. Sodium is highly preferred.

Exemplary compounds include but are not limited to such salts as sodium 2,3-dihydroxypropyltrithiocarbonate
potassium 2,11,12-trihydroxydodecyltrithiocarbonate
potassium tris(hydroxymethyl)methyltrithiocarbonate and the like and mixtures thereof. Sodium 2,3-dihydroxypropyltrithiocarbonate is presently preferred because it has been tested and shown to be an effective depressant.

These and similar compounds function as mineral sulfide depressants and are used with solid ores, concentrates or cleaners. The materials are basically depressants for Cu, Fe and Mo sulfides but other mineral sulfides such as those based on Pb, Zn, Ni, etc. are considered within the scope of this invention. Exemplary ores include the following:

| | |
|---|---|
| Molybdenum-Bearing Ores | |
| Molybdenum | $MoS_2$ |
| Wulfenite | $PbMoO_4$ |
| Powellite | $Ca(MO,W)O_4$ |
| Ferrimolybdite | $Fe_2Mo_3O_{12}.8H_2O$ |
| Copper-Bearing Ores | |
| Covallite | $CuS$ |
| Chalcocite | $Cu_2S$ |
| Chalcopyrite | $CuFeS_2$ |
| Bornite | $Cu_5FeS_4$ |
| Cubanite | $Cu_2SFe_4S_5$ |
| Valerite | $Cu_2Fe_4S_7$ or $Cu_3Fe_4S_7$ |
| Enargite | $Cu_3(As,Sb)S_4$ |
| Tetrahedrite | $Cu_3SbS_2$ |
| Tennanite | $Cu_{12}As_4S$ |
| Stannite | $Cu_2S.FeS.SnS_2$ |
| Bournonite | $PbCuSbS_3$ |
| Lead-Bearing Ore: | |
| Galena | $PbS$ |
| Antimony-Bearing Ore: | |
| Stibnite | $Sb_2S_3$ |
| Kermesite | $Sb_2S_2O$ |
| Zinc-Bearing Ore: | |
| Sphalerite | $ZnS$ |
| Silver-Bearing Ore: | |
| Argentite | $Ag_2S$ |
| Stephanite | $Ag_5SbS_4$ |

-continued

| | |
|---|---|
| Polybasite | $9Ag_2S.Sb_2S_3$ |
| Iron-Bearing Ore: | |
| Pyrite | $FeS_2$ |
| Pyrrohotite | $Fe_5S_6$ to $Fe_{16}S_{17}$ |
| Arsenopyrite | FeAsS |
| Marmatite | (ZnFe)S |
| Nickel-Bearing Ore: | |
| Millerite | NiS |
| Pentlandite | (FeNi)S |
| Ullmannite | NiSbS |

The amount of trithiocarbonate treating agent employed as a depressant for one or more minerals can vary widely. Generally, the quantity used depends on the amount of flotation or collecting agent employed, the flotation technique used, and on the amount and kinds of minerals present in the ore. Generally, from 0.005 to 20 lbs of treating agent based on trithiocarbonate component per ton of ore is employed, usually from about 0.01 to about 5 lbs per ton, preferably from about 0.1 to about 1 lb per ton. The treating agent is effective under both acidic and basic conditions such as over a pH range of 5 to 11. In one preferred embodiment of the instant invention trithiocarbonates are used to suppress the flotation of copper and iron from ores containing them.

The aqueous treating agent obtained from the reaction of the metal salt of the thiol with $CS_2$ is the preferred treating agent of the invention for use as a depressant composition in a flotation process.

Generally, the flotation process comprises carrying out a minerals flotation with a depressant composition present, with the depressant composition being represented by the formula:

$$(HO)_n-R'-CH_2-S-\overset{\overset{\displaystyle S}{\|}}{C}-S-Y$$

where n, R' and Y are previously defined.

Generally, the flotation process will utilize a composition comprising the treating agent, water, and the mineral material. The depressants of the present invention can be used to depress iron, copper and/or lead in the presence of molybdenum. The depressants of the invention are also effective to depress sulfides in the presence of coal, and thus may also have utility in coal beneficiation. In ores, the metals are usually in a solid sulfided state and form a slurry, which can be finely divided, as in a pulp. For example, the invention can be employed to process an ore slurry containing high copper values. The invention can also be employed to process a concentrate, such as a concentrate which contains high molybdenum values. Generally, the solids to be processed will be present as a slurry in water which contains the treating agent with the treating agent being present in an amount of between about 0.005 and about 20 pounds per ton of the solids. The slurry usually contains between about 10 and 75 percent solids preferably in the range of 15–60 weight percent solids, depending on the processing stage. Preferably, the trithiocarbonate or derivative is present in the composition in an amount in the range of between about 0.01 to about 5 pounds per ton of solids. Even more preferably, the trithiocarbonate is present in an amount in the range of between about 0.1 and about 5 pounds per ton of the solids.

The flotation process usually involves the steps of:

(a) mixing crushed or ground mineral material with water and the treating agent defined above to establish a pulp, (b) aerating the pulp to produce a froth and a pulp, (c) separating the froth from the pulp and producing a concentrate product and a tail product, and (d) recovering minerals from the so separated concentrate and/or tail product.

The depressant composition of the invention can also be employed with frothers and flotation agents.

Examples of frothers that can be used in addition to the collector compositions defined above are polyoxyalkylene glycols and their corresponding methyl or ethyl ethers having broadly a molecular weight of about 400 to about 1000, and preferably a molecular weight in the range of about 420 to about 780. Particularly polypropylene glycols and their ethers having molecular weights of e.g., 400, 425, 750 or 900 can be used. Also polybutylene glycol and polypentylene glycol are useful materials. Examples of other frothers that may be used are alcohols such as methyl isobutyl carbinol, pine oil, phenols, fatty acids and cresylic acid. Examples of suitable flotation agents are organic xanthates, organic trithiocarbonates, amines, dithiocarbamates, fuel oils, aromatic oils and the like, generally in an amount of 0.005–0.5 pounds per ton of solids. Preferably frother and an oily flotation agent are used together.

The inventive depressant can be used together with other depressant or depression steps if desired. For example, the depressant composition defined above can be used after a surface treatment of the solids, such as after heating or oxidation of a concentrate or with sulfuric acid, and/or with additional depressants, such as sodium cyanide, sodium ferrocyanide, lime and zinc sulfate, in the treatment of an ore.

Any froth flotation apparatus can be used in this invention. The most commonly used commercial flotation machines are the Agitair (Galigher Co.), Denver D-2 (Denver Equipment Co.), and the .Fagergren (Western Machinery Co.). Smaller, laboratory scale apparatus such as the Hallimond cell can also be used.

The instant invention was demonstrated in tests conducted at ambient room temperature and atmospheric pressure. However, any temperature or pressure generally employed by those skilled in the art is within the scope of this invention.

EXAMPLE I

This example describes the preparation of the inventive trithiocarbonate compound described herein. To a 3-neck glass flask fitted with a condenser, stirrer, thermometer and dropping funnel was added 96 milliliters of water and 14 grams (0.35 mole) of sodium hydroxide. After cooling to below 50° C., 36.1 grams (0.33 mole) of 3-mercapto-1,2-propanediol was slowly added with stirring over a 10 to 20 minute period. The mixture was cooled to below 45° C. and 25.4 grams (0.33 mole) of carbon disulfide was slowly added over a 30 minute period. The cloudy mixture was maintained with stirring at 45° C. for about 1.5 hours at which time the solution became hazy and orange-colored. The solution was cooled to room temperature and bottled. The solution was estimated to be 40 weight percent of sodium 3-(thiocarbonyldithio)-1,2-propanediol also referred herein as sodium 2,3-dihydroxypropyltrithiocarbonate.

EXAMPLE II

This example discloses the use of the trithiocarbonate derivative described in Example I as an ore flotation reagent, particularly as a mineral sulfide depressant. To a 3 liter capacity Agitar LA 500 flotation cell was added 415 milliliters of a copper/molybdenum-containing agitated pulp (about 600 grams of solid-Anamax Mining Co.) and enough water to make about 30 weight percent aqueous mixture. The mixture had a natural pH of 10.4. The depressant to be evaluated was then added and the mixture conditioned for about 2 minutes at 1200 rpm and then floated for 5 minutes. The concentrate was filtered, dried and analyzed. The flotation was repeated except before the depressant was added there was enough sulfuric acid added to reduce the pH between 6.0 and 7.0. The evaluation listed in Table I was conducted in the absence of a depressant, in the presence of 3 depressants (including the inventive depressant), and in the presence of a Mo collector (Molyflo, an oily Mo collector from Phillips Petroleum Co.). The results indicate the inventive trithiocarbonate acts as a mineral sulfide depressant in either acid or basic conditions and appears to be superior in depression to any of the other reagents tested.

TABLE I

Effect of Various Materials on Mineral Sulfide Depression

| Run No. | Reagent | lb/ Ton | % Recovery pH 6.0–7.0 Cu | Fe | Mo | pH 10.4 Cu | Fe | Mo |
|---|---|---|---|---|---|---|---|---|
| Control: | | | | | | | | |
| 1 | None | — | 5.1 | 4.3 | 82.5 | 25.7 | 23.5 | 27.8 |
| 2 | Molyflo[a] | 0.14 | 6.3 | 5.3 | 84.8 | 28.5 | 28.2 | 32.7 |
| 3 | Disodium Carboxymethyl Trithiocarbonate, 40 Wt. % Aq. | 0.8 | 3.0 | 4.0 | 6.3 | 3.4 | 4.0 | 57.9 |
| 4 | Trisodium Succinyl Trithiocarbonate,[b] 40 Wt. % Aq. | 0.8 | 2.8 | 3.3 | 78.5 | 3.0 | 3.2 | 72.1 |
| Invention: | | | | | | | | |
| 5 | Sodium 2,3-Dihydroxy-propyl Trithiocarbonate,[b] 40 Wt. % Aq. | 0.8 | 3.0 | 2.9 | 4.0 | 3.8 | 4.3 | 10.0 |

[a]An oily moly collector from Phillips Petroleum Co.
[b]Also referred herein as sodium 3-(thiocarbonyldithio)-1,2-propanediol from Example I.

We claim:

1. A composition comprising water and a trithiocarbonate represented by the formula:

$$(HO)_n-R'-CH_2-S-\overset{S}{\overset{\|}{C}}-S-Y$$

where R' is a $C_2$–$C_{21}$ organic moiety, Y is a Group IA or IIA metal ion or an ammonium ion and n is an integer of from 2 to 22.

2. A composition as in claim 1 further comprising an aqueous slurry of a solids-containing mineral material.

3. A composition as in claim 2 wherein the slurry contains between about 10 and about 75 weight percent solids and the trithiocarbonate is present in an amount of between about 0.005 and about 5 pounds per ton of solids.

4. A composition as in claim 3 wherein the trithiocarbonate is selected from the group consisting of sodium 2,3-dihydroxypropyltrithiocarbonate, and potassium tris(hydroxymethyl)methyltrithiocarbonate.

5. A composition as in claim 4 wherein the trithiocarbonate is present in an amount in the range of between about 0.1 and about 5 pounds per ton of solids.

6. A composition as in claim 5 containing 15–60 weight percent solids wherein the solids comprise molybdenum and metal sulfides.

7. A composition as in claim 6 wherein the trithiocarbonate comprises an ammonium or Group IA metal salt of 2,3-dihydroxypropyltrithiocarbonate.

8. A process for depressing certain minerals in a minerals containing mixture in a flotation operation, said process comprising carrying out a flotation with a depressant composition present, said depressant composition resulting from the chemical combination of $(HO)_n$-$R'CH_2SH+CS_2+YOH$ in an aqueous reaction medium, n is an integer of from 2 to 22, R is a $C_1$–$C_{21}$ organic moiety, and Y is a Group IA or IIA metal ion or ammonium ion.

9. Process in accordance with claim 8 wherein said minerals to be depressed comprise sulfided minerals.

10. Process as in claim 9 wherein said minerals are to be depressed from an aqueous coal slurry.

11. Process as in claim 10 wherein the depressant composition results from the chemical combination of sodium hydroxide, $CS_2$ and 3-mercapto-1,2-propanediol.

12. In a process for the recovery of mineral values from a froth from an aqueous slurry containing the ore or a concentrate from the ore containing the mineral, wherein the slurry further contains sulfides of at least one of copper, iron and lead, the improvement comprising employing in the aqueous slurry at least one depressant represented by the formula:

$$CH_2OH-\overset{(OH)_n}{\overset{|}{R}}-CHOH-CH_2-S-\overset{S}{\overset{\|}{C}}-S-Y$$

where R present is a $C_0$ to $C_{20}$ organic moiety and Y is a Group IA or IIA metal ion or an ammonium ion and n is an integer of from 0 to 3.

13. A process as in claim 12 wherein the depressant is selected from the group consisting of sodium 2,3-dihydroxypropyltrithiocarbonate and potassium tris(hydroxymethyl)methyltrithiocarbonate.

14. A process as in claim 13 wherein the depressant is employed in the range of 0.05 to about 5 pounds per ton of ore or concentrate.

15. A process as in claim 14 wherein the depressant is employed in the range of 0.1 to about 5 pounds per ton of ore or concentrate.

16. A process as in claim 14 wherein the depressant comprises sodium 2,3-dihydroxypropyltrithiocarbonate.

17. An aqueous composition suitable for use as a treating agent in an ore flotation process, said treating agent made by a process comprising:

(a) reacting, in an aqueous medium, ammonium hydroxide or an alkali metal hydroxide with a material represented by the formula $(HO)_nR'CH_2SH$ where n is an integer of 0 to 22 and R' is a $C_2$–$C_{22}$ organic moiety, to form a reaction product, and (b) adding to the reaction product carbon disulfide in an amount sufficient to effect formation of the treating agent.

18. An aqueous composition as in claim 17 wherein sodium hydroxide is reacted with 3-mercapto-1,2-propanediol to form the reaction product.

19. A compound comprising sodium 2,3-dihydroxypropyltrithiocarbonate.

* * * * *